(12) United States Patent
Wang et al.

(10) Patent No.: US 10,267,791 B2
(45) Date of Patent: Apr. 23, 2019

(54) BIOLOGICAL TEST STRIP WITH ISOLATION STRUCTURE

(71) Applicant: VIDA BIOTECHNOLOGY CO., LTD, Taichung (TW)

(72) Inventors: Wen-Chih Wang, Taichung (TW); Bing-Chen Gu, Taichung (TW); Yu-Han Dai, Taichung (TW)

(73) Assignee: VIDA BIOTECHNOLOGY CO., LTD, Taichung (TW)

( * ) Notice: Subject to any disclaimer, the term of this patent is extended or adjusted under 35 U.S.C. 154(b) by 194 days.

(21) Appl. No.: 15/586,728

(22) Filed: May 4, 2017

(65) Prior Publication Data

US 2017/0322205 A1    Nov. 9, 2017

(30) Foreign Application Priority Data

May 5, 2016   (TW) .............................. 105113948 A

(51) Int. Cl.
 *G01N 33/543*     (2006.01)
(52) U.S. Cl.
 CPC .............................. *G01N 33/5438* (2013.01)
(58) Field of Classification Search
 USPC ..... 204/400, 403.01, 403.03, 412; 422/82.01
 See application file for complete search history.

(56) References Cited

U.S. PATENT DOCUMENTS

| | | | | |
|---|---|---|---|---|
| 4,897,173 A | * | 1/1990 | Nankai | C12Q 1/004 204/403.05 |
| 2005/0265897 A1 | * | 12/2005 | Maruo | C12Q 1/005 422/82.01 |
| 2010/0025264 A1 | * | 2/2010 | Yuan | C12Q 1/005 205/777.5 |
| 2010/0291611 A1 | * | 11/2010 | Bolbot | G01N 33/54386 435/29 |
| 2011/0031118 A1 | * | 2/2011 | Machida | G01N 27/3272 204/403.14 |
| 2011/0272295 A1 | * | 11/2011 | Lee | G01N 27/3272 205/792 |
| 2012/0135509 A1 | * | 5/2012 | Hall | C12Q 1/001 435/287.1 |
| 2013/0270113 A1 | | 10/2013 | Huang | |
| 2014/0209485 A1 | * | 7/2014 | Ohgami | G01N 27/333 205/789 |

(Continued)

*Primary Examiner* — Christopher L Chin
(74) *Attorney, Agent, or Firm* — Muncy, Geissler, Olds & Lowe, P.C.

(57) ABSTRACT

A biological test strip with isolation structure includes a substrate having a testing portion and a measuring portion; an electrode disposed on the substrate and including an operation electrode and an auxiliary electrode, the operation electrode having a first operating end and a first reading end, the auxiliary electrode having a second operating end and a second reading end; a first flow confining member surrounding the first operating end; and a second flow confining member surrounding the first flow confining member and the second operating end, with a height of the second flow confining member larger than a height of the first flow confining member. Therefore, the flowing scope of the dropped liquid is confined, so as to fix the square measure of the dropped liquid contacting the electrode and thereby improve the analysis repeatability.

5 Claims, 6 Drawing Sheets

(56) References Cited

U.S. PATENT DOCUMENTS

| | | | | |
|---|---|---|---|---|
| 2014/0251826 A1* | 9/2014 | Koelker | ................. | C12Q 1/006 |
| | | | | 205/777.5 |
| 2014/0332377 A1* | 11/2014 | Su | ........................ | G01N 27/327 |
| | | | | 204/403.01 |
| 2016/0116427 A1* | 4/2016 | Laurenson | ........... | G01N 27/327 |
| | | | | 422/82.01 |

* cited by examiner

BIOLOGICAL TEST STRIP WITH ISOLATION STRUCTURE

BACKGROUND OF THE INVENTION

1. Field of the Invention

The present invention relates to biological test strips, and more particularly, to a biological test strips with isolation structure.

2. Description of the Related Art

Medical advancement nowadays prolongs the longevity of human being. However, contagious diseases have been gradually replaced by chronical diseases, which have become one of the main causes of death. By analyzing the relative values of blood sugar, cholesterol, and uric acid, potential chronical diseases in the organism are allowed to be identified in advance. Further, the present invention is also usable for conducting, for example, protein and DNA analysis, and measuring various biological values.

A conventional test strip, as disclosed by US US20130270113 "Electrochemical strip and manufacturing method thereof", comprises a substrate, a printed conductive plate, a first metal layer, a second metal layer, a third metal layer, a fourth metal layer, and an insulator layer that are stacked in layers, with reaction material coated on the fourth electrode, so as to conduct an electrochemical reaction and thereby produces electronic current signals, which are subsequently transmitted to a measuring machine for being calculated and transformed into concentration information of a target substance.

However, such test strip is not provided with any blocking mechanism for confining the flowing scope of the reaction material and target substance. If the target substance is a fluid with aggregation property, the fluid is able to be controlled by surface tension and concentrated at the specific electrode position of the test strip. But, if the target substance is a fluid comprising non-aggregating component such as alcohol, the reaction material and the target substance will randomly spread on the test strip and fail to be concentrated at the specific electrode position, causing a varying square measures of the reaction material and target substance contacting the electrode from time to time, whereby the square measures of the electrons and ions exchange area are unable to remain consistent. As a result, noise signals possibly occur to affect the measuring repeatability. Therefore, it is desired for the industry to improve the repeatability of the data measurement.

SUMMARY OF THE INVENTION

For improving the issues above, a biological test strip with isolation structure is disclosed, which is capable of preventing the liquid from contacting the electrodes with varying square measure thereof from time to time during the analyzing process, so as to enhance the analysis repeatability.

For achieving the aforementioned objectives, an embodiment of the present invention provides a biological test strip with isolation structure, comprising:

a substrate, including a testing portion and a measuring portion;

an electrode disposed on the substrate and further including an operation electrode and an auxiliary electrode, the operation electrode provided with a first operating end disposed on the testing portion and a first reading end disposed on the measuring portion, the auxiliary electrode provided with a second operating end disposed on the testing portion and a second reading end disposed on the measuring portion;

a first flow confining member disposed on the measuring portion and surrounding the first operating end of the operation electrode; and a second flow confining member disposed on the testing portion and further surrounding the first flow confining member and the second operating end of the auxiliary electrode, a height of the second flow confining member against the substrate is larger than a height of the first flow confining member against the substrate.

With such configuration, the first flow confining member and the second flow confining member are provided, such that a liquid dropped upon the testing portion is confined in the first flow confining member and thereby only contacts the first operating end, or is alternatively confined in the second flow confining member and thereby contacts the second operating end of the auxiliary electrode and the first operating end of the operation electrode. Therefore, the liquid contacts the electrodes by a fixed square measure, so as to lower the occurrence of noise signals and improve the analysis repeatability.

DETAILED DESCRIPTION OF THE INVENTION

The aforementioned and further advantages and features of the present invention will be understood by reference to the description of the preferred embodiment in conjunction with the accompanying drawings where the components are illustrated based on a proportion for explanation but not subject to the actual component proportion.

Figure 1:
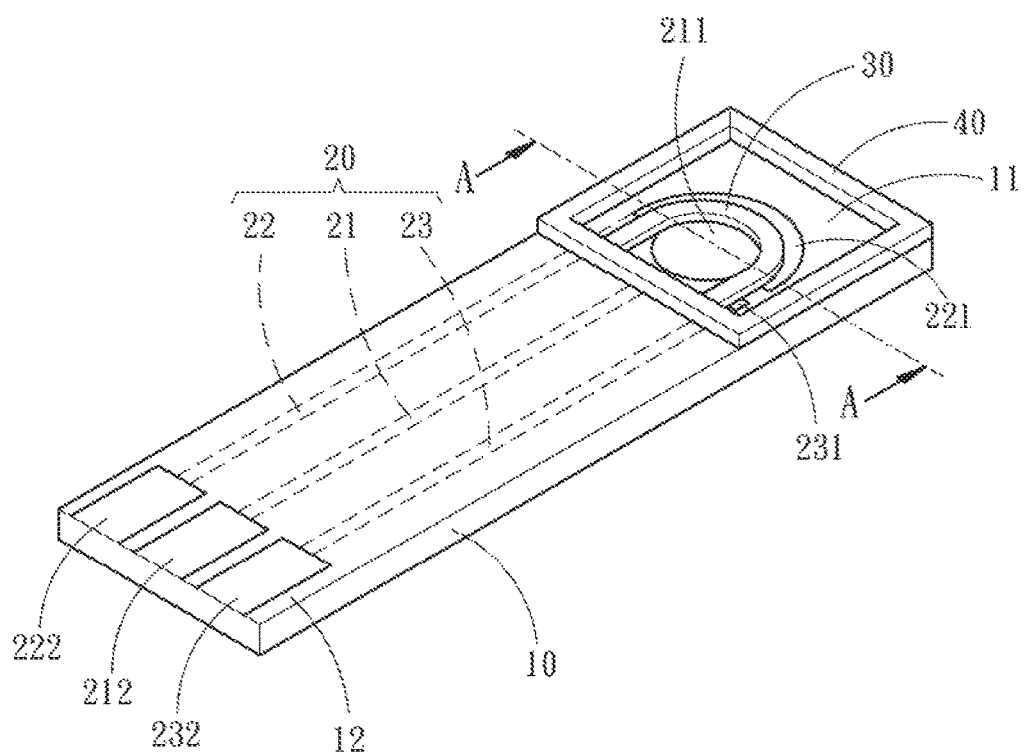
FIG. 1 is a perspective view of the biological test strip in accordance with a preferred embodiment of the present invention.
Figure 2:
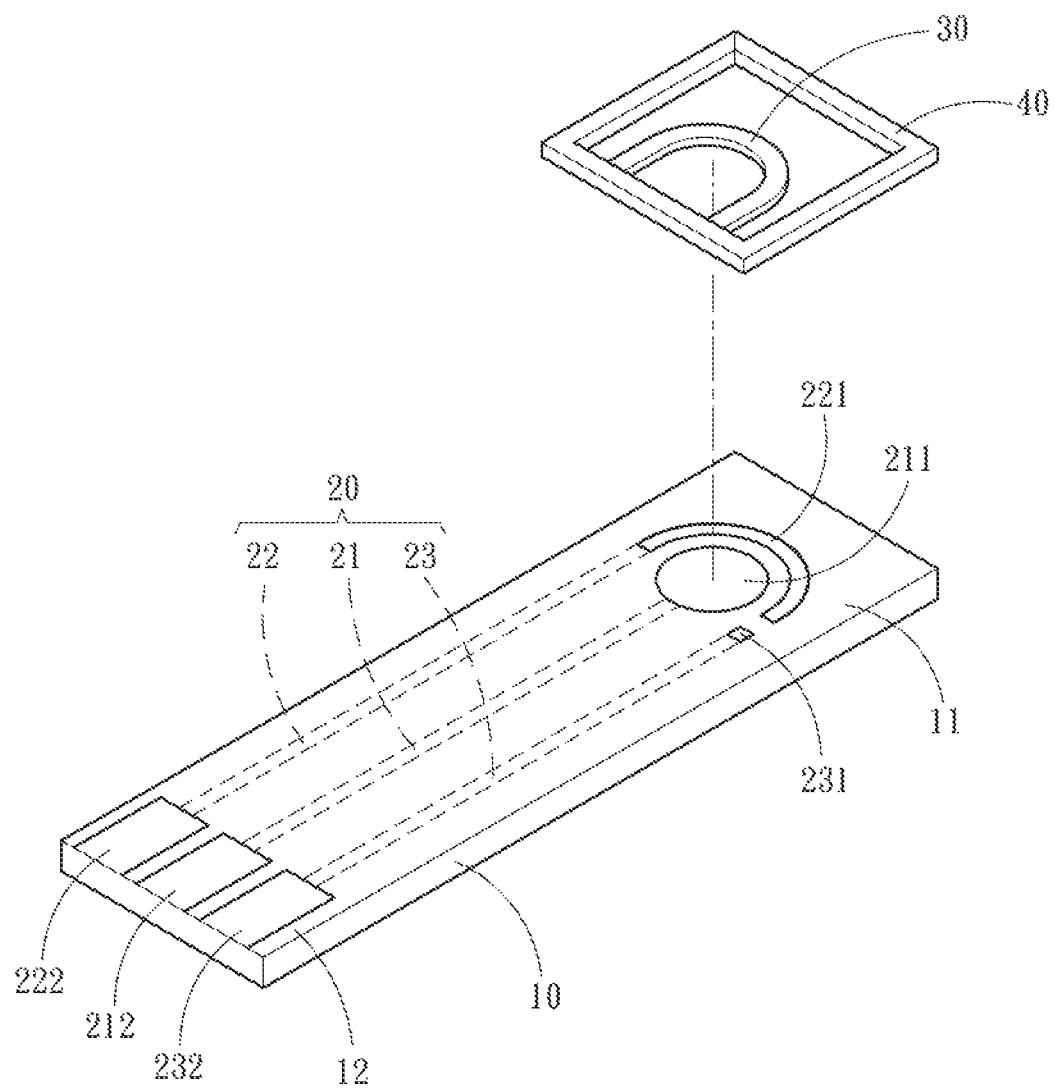
FIG. 2 is an exploded view of the biological test strip in accordance with a preferred embodiment of the present invention.

Referring to FIG. 1 to FIG. 2, the present invention provides an embodiment of a biological test strip with isolation structure, comprising a substrate 10, an electrode 20 disposed on the substrate 10, a first flow confining member 30, and a second flow confining member 40.

The substrate 10 includes a testing portion 11 and a measuring portion 12. The electrode 20 includes an operation electrode 21 and an auxiliary electrode 22. The operation electrode 21 is provided with a first operating end 211 disposed on the testing portion 11 and a first reading end 212 disposed on the measuring portion 12. The auxiliary electrode 22 is provided with a second operating end 221 disposed on testing portion 11 and a second reading end 222 disposed on the measuring portion 12. The first flow confining member 30 is disposed on the testing portion 11 and surrounds the first operating end 211 of the operation electrode 21. The second flow confining member 40 is disposed on the testing portion 11 and further surrounds the first flow confining member 30 and the second operating end 221 of the auxiliary electrode 22. In an embodiment of the present invention, the first flow confining member 30 and the second flow confining member 40 both extend from the substrate 10. Also, the height of the second flow confining member 40 is larger than the height of the first flow confining member 30. In other words, the height of the second flow confining member 40 against the substrate 10 is larger than the height of the first flow confining member 30 against the substrate 10. In an embodiment of the present invention, the height of the first flow confining member 30 ranges from 0.25 mm to 0.5 mm, and the height of the second flow confining member 40 is larger than 0.8 mm.

Furthermore, the electrode 20 includes a reference electrode 23 which is also surrounded by the second flow confining member 40 and comprises a third operating end 231 disposed on the testing portion 11 and a third reading end 232 disposed on the measuring portion 12. The first flow confining member 30 and the second flow confining member 40 are formed of an insulator material which is not reacting with other matters. In an embodiment of the present invention, the first flow confining member 30 and the second flow confining member 40 are formed of a material of silica gel.

In an embodiment of the present invention, the central portion of the electrode 20 is covered. In particular, the section between the first operating end 211 and the first reading end 212, the section between the second operating end 221 and the second reading end 222, and the section between the third operating end 231 and the third reading end 232 are covered.

Figure 3:
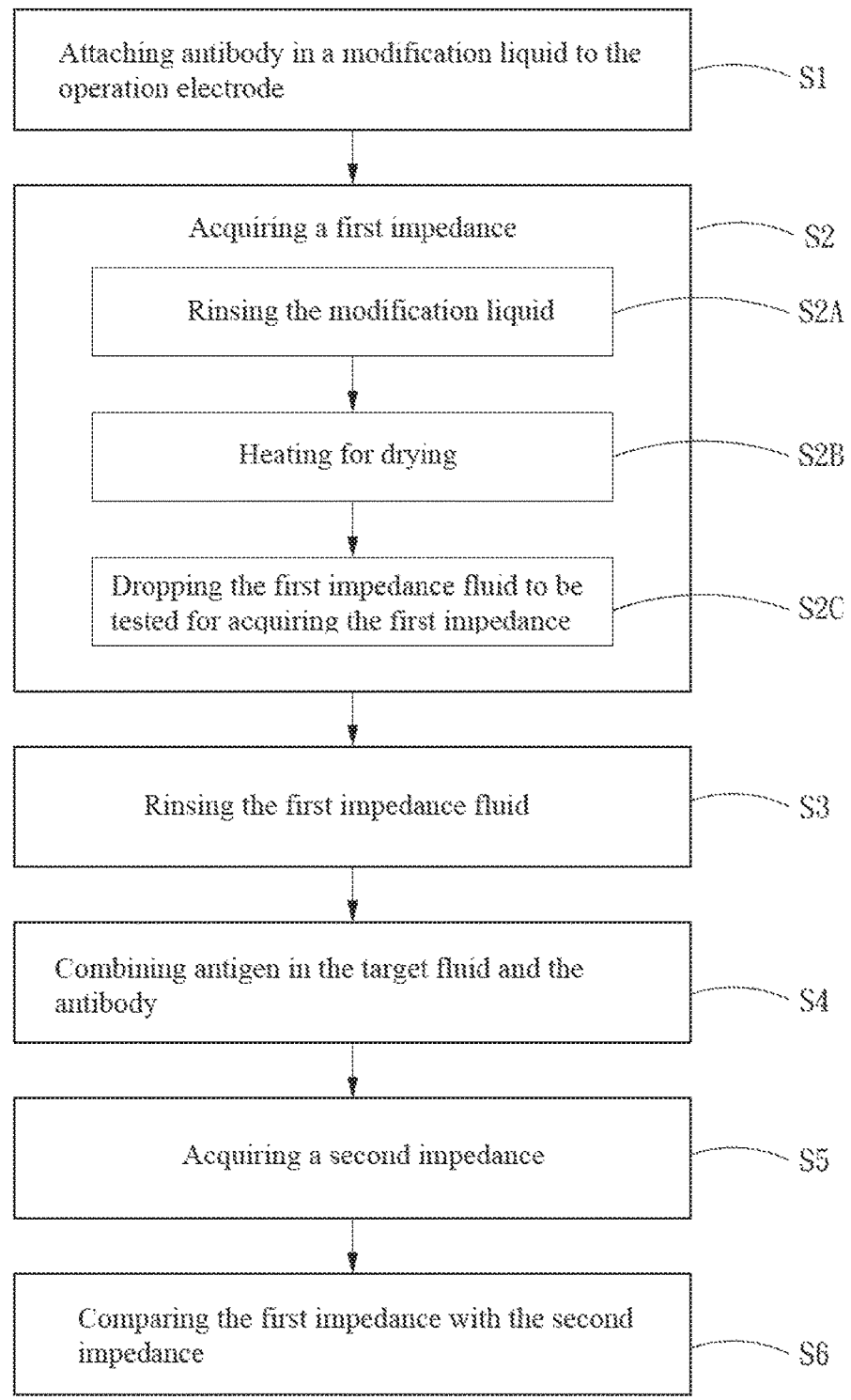
FIG. 3 is a flow chart illustrating the operation of the biological test strip.

Referring to FIG. 3, an embodiment of the operating process of the present invention is illustrated. Also, for clearly illustrating the operating method of the present invention, the operating process in FIG. 3 is further illustrated along with the content from FIG. 4A to FIG. 4E, which schematically display the operating status embodiments of the present invention with cross-sectional views taken along line A-A in FIG. 1.

The operating process of the present invention, as illustrated by the flow chart of FIG. 3, comprises following steps: attaching antibody 51 in a chemical modification liquid 50 to the operation electrode 21 S1; acquiring a first impedance S2; rinsing the first impedance fluid S3; combining antigen 71 in the target fluid 70 and the antibody 51 S4; acquiring a second impedance S5; and comparing the first impedance with the second impedance S6.

Figure 4A:
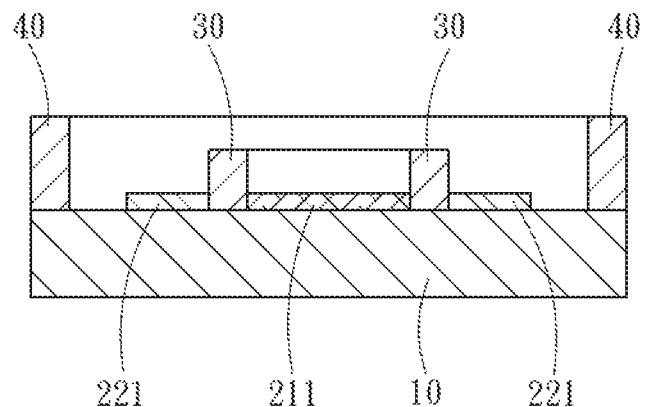
FIG. 4A to 4E are sectional views illustrating the operation of the biological test strip.
Figure 4B:
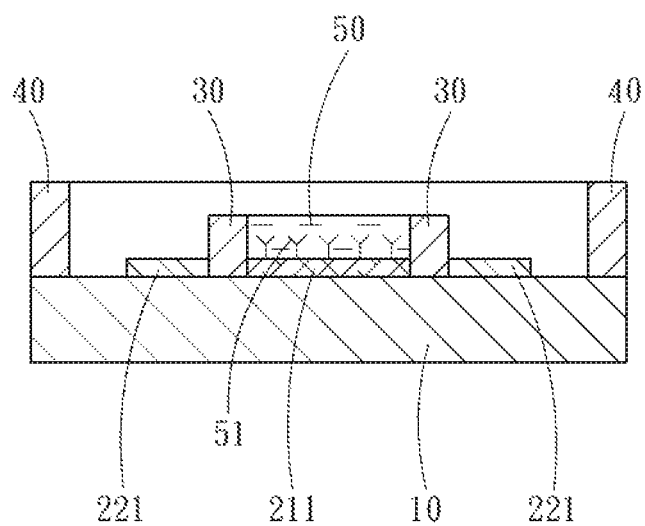

In the step S1, referring to FIG. 4A and FIG. 4B, the chemical modification liquid 50 is dropped in the first flow confining member 30. Due to the structure of the first flow confining member 30, the chemical modification liquid 50 only contacts the first operating end 211, such that the square measure of the chemical modification liquid 50 contacting the electrode 20 is fixed, and the chemical modification liquid 50 is prevented from overflowing the first operating end 211 and affecting the reacting molecular amounts. After a cultivation period, plural antibodies 51 in the chemical modification liquid 50 are attached to the first operating end 211.

Figure 4C:
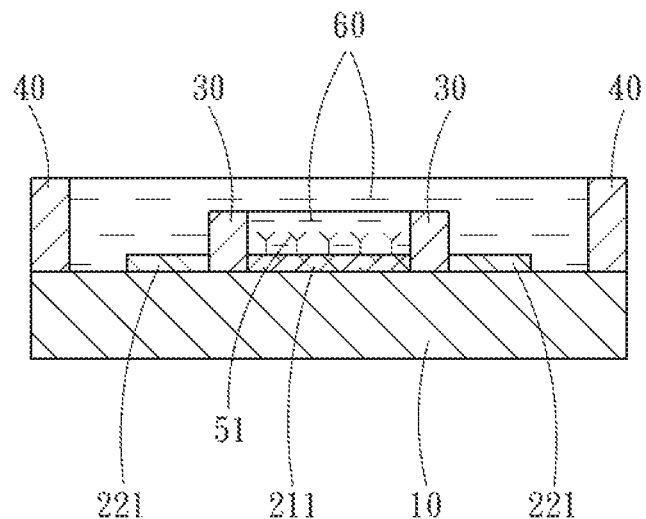

In the step S2, referring to FIG. 2 and FIG. 4C, the chemical modification liquid 50 in the first flow confining member 30 is rinsed. Then, a first impedance fluid 60 is dropped in the first flow confining member 30 and the second flow confining member 40. Since the height of the first flow confining member 30 is lower than the height of the second flow confining member 40, the first impedance fluid 60 is allowed to flow in the first flow confining member 30 and the second flow confining member 40 under an identical concentration gradient. Also, the first impedance fluid 60 only contacts the first operating end 211, the second operating end 221, and the third operating end 231 surrounded by the second flow confining member 40.

Therefore, the square measure of the first impedance fluid 60 contacting the electrode 20 is fixed. Further through a testing machine electrically connected with the first reading end 212, the second reading end 222, and the third reading end 232, a first impedance is acquired.

In an embodiment, the step S2 further includes following steps: rinsing the testing portion 11 with a cleaning fluid S2A for rinsing the chemical modification liquid 50 in the first flow confining member 30; heating for drying S2B, so as to remove any cleaning fluid residual on the testing portion 11; and dropping the first impedance fluid 60 in the first flow confining member 30 and the second flow confining member 40, and allowing the first impedance fluid 60 to flow through the first flow confining member 30 and the second flow confining member 40, so as to testing through the testing machine for acquiring the first impedance S2C.

In the step S3, the first impedance fluid 60 in the first flow confining member 30 and the second flow confining member 40 is rinsed, and the testing portion 11 is dried.

Figure 4D:
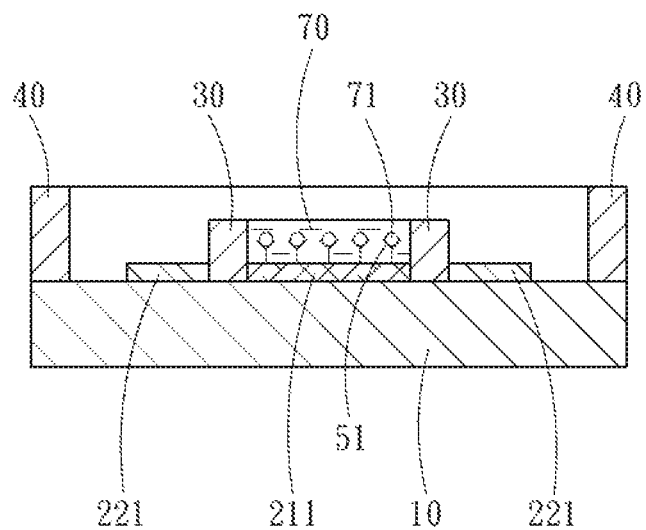

In the step S4, referring to FIG. 2 and FIG. 4D, a target fluid 70 is dropped in the first flow confining member 30. The first flow confining member 30 allows the target fluid 70 to only contact the first operating end 211, such that the square measure of the target fluid 70 contacting the electrode 20 is fixed. After a cultivation period, plural antigens 71 in the target fluid 70 are combined with the antibodies 51.

Figure 4E:
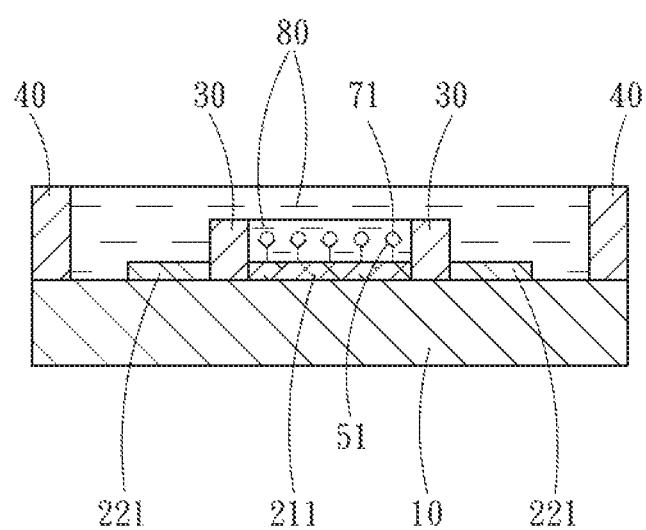

In the step S5, referring to FIG. 4E, the target fluid 70 in the first flow confining member 30 is rinsed and dried. Next, a second impedance fluid 80 is dropped in the first flow confining member 30 and the second flow confining member 40. Through the testing process conducted by the testing machine, a second impedance is acquired. In this step, the second impedance fluid 80 is also allowed to flow in the first flow confining member 30 and the second flow confining member 40 under an identical concentration gradient. Also, the square measure of the second impedance fluid 80 contacting the electrode 20 is fixed. Therefore, under an identical usage amount in the analysis, the square measures of the electrons and ions exchange area are assured of remaining consistent from time to time, so as to lower the occurrence of noise signals and improve the analysis repeatability.

In the step S6, the first impedance and the second impedance are compared to acquiring a testing result. For example, if the first impedance is 10 ohm while the second impedance is 18 ohm, a difference of 8 ohm is acquired. With further calculation, the amount of combination between the antibodies 71 and the antigens 51 is acquired.

With the foregoing configuration, the present invention achieves following advantages.

By use of the first flow confining member 30, the chemical modification liquid 50 and the target fluid 70 only contact the first operating end 211 of the operation electrode 21 by a fixed squared measure, and are prevented from outflowing the first operating end 211 and affecting the reacting molecular amounts.

By use of the second flow confining member 40, the first impedance fluid 60 and the second impedance fluid 80 only contact the first operating end 211, the second operating end 221, and the third operating end 231 by a fixed square measure. Also, the square measures of the electrons and ions exchange area are assured of remaining consistent from time to time during the analysis, so as to lower the occurrence of noise signals and improve the analysis repeatability.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A biological test strip with isolation structure, comprising:
   a substrate including a testing portion and a measuring portion;
   an electrode disposed on the substrate and further including an operation electrode and an auxiliary electrode, the operation electrode provided with a first operating end disposed on the testing portion and a first reading end disposed on the measuring portion, the auxiliary electrode provided with a second operating end disposed on the testing portion and a second reading end disposed on the measuring portion;
   a first flow confining member disposed on the measuring portion and surrounding the first operating end of the operation electrode; and
   a second flow confining member disposed on the testing portion and further surrounding the first flow confining member and the second operating end of the auxiliary electrode, a height of the second flow confining member against the substrate is larger than a height of the first flow confining member against the substrate.

2. The biological test strip of claim 1, wherein the height of the first flow confining member ranges from 0.25 mm to 0.5 mm, and the height of the second flow confining member is larger than 0.8 mm.

3. The biological test strip of claim 1, wherein the first flow confining member and the second flow confining member are formed of an insulator material.

4. The biological test strip of claim 3, wherein the insulator material is silica gel.

5. The biological test strip of claim 1, wherein the electrode includes a reference electrode which is also surrounded by the second flow confining member, the reference electrode further including a third operating end disposed on the testing portion and a third reading end disposed on the measuring portion.

* * * * *